United States Patent [19]

Phillips

[11] Patent Number: 4,932,965
[45] Date of Patent: Jun. 12, 1990

[54] ARTIFICIAL VALVE, AND NEEDLE AND SUTURE HOLDER AND METHOD OF USING SAME

[76] Inventor: Steven J. Phillips, 5300 Woodland Ave., Des Moines, Iowa 50312

[21] Appl. No.: 286,625

[22] Filed: Dec. 19, 1988

[51] Int. Cl.⁵ .................... A61F 2/24; A61B 17/00
[52] U.S. Cl. .................................. 623/2; 606/1
[58] Field of Search .......... 623/2; 128/303 R, 334 R; 606/1

[56] References Cited

U.S. PATENT DOCUMENTS

| | | | |
|---|---|---|---|
| 3,143,742 | 8/1964 | Cromie | 623/2 |
| 3,371,352 | 3/1968 | Siposs et al. | 623/2 |
| 3,409,013 | 11/1968 | Berry | 128/303 R |
| 3,417,777 | 12/1968 | De Balsac et al. | 137/525 |
| 3,574,865 | 4/1971 | Hamaker | 623/2 |
| 3,714,671 | 2/1973 | Edwards et al. | 623/2 |
| 3,755,823 | 9/1973 | Hancock | 623/2 |
| 3,805,301 | 4/1974 | Liebig | 623/1 |

FOREIGN PATENT DOCUMENTS 207339  7/1968  U.S.S.R. .................. 623/2

Primary Examiner—Ronald L. Frinks
Attorney, Agent, or Firm—Zarley, McKee, Thomte, Voorhees & Sease

[57] ABSTRACT

An artificial valve is provided which includes a holder for the sutures and needles. The holder positions the needles away from the valve but in a position where they may be readily reached during the valve replacement operation. The sutures are prethreaded through the valve sewing ring and are color coded for identification purposes when opposite ends are being tied together at the completion of the implantation procedure.

11 Claims, 2 Drawing Sheets

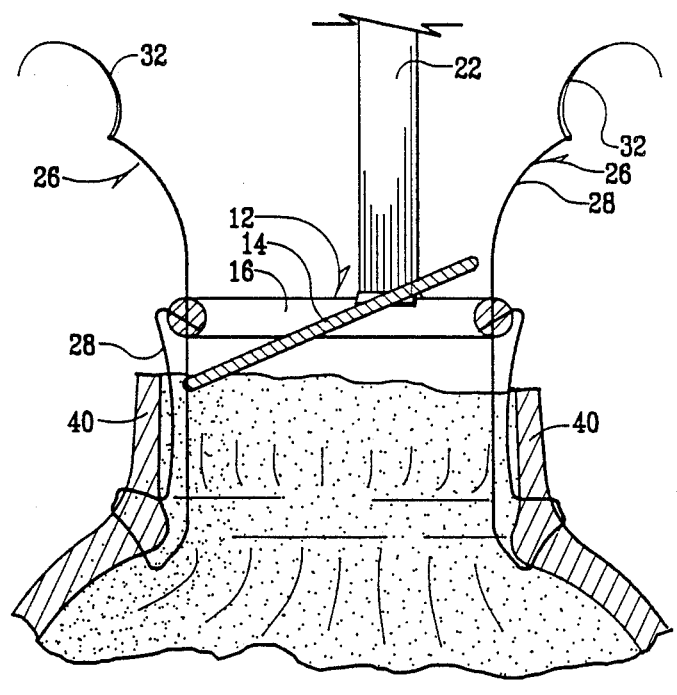
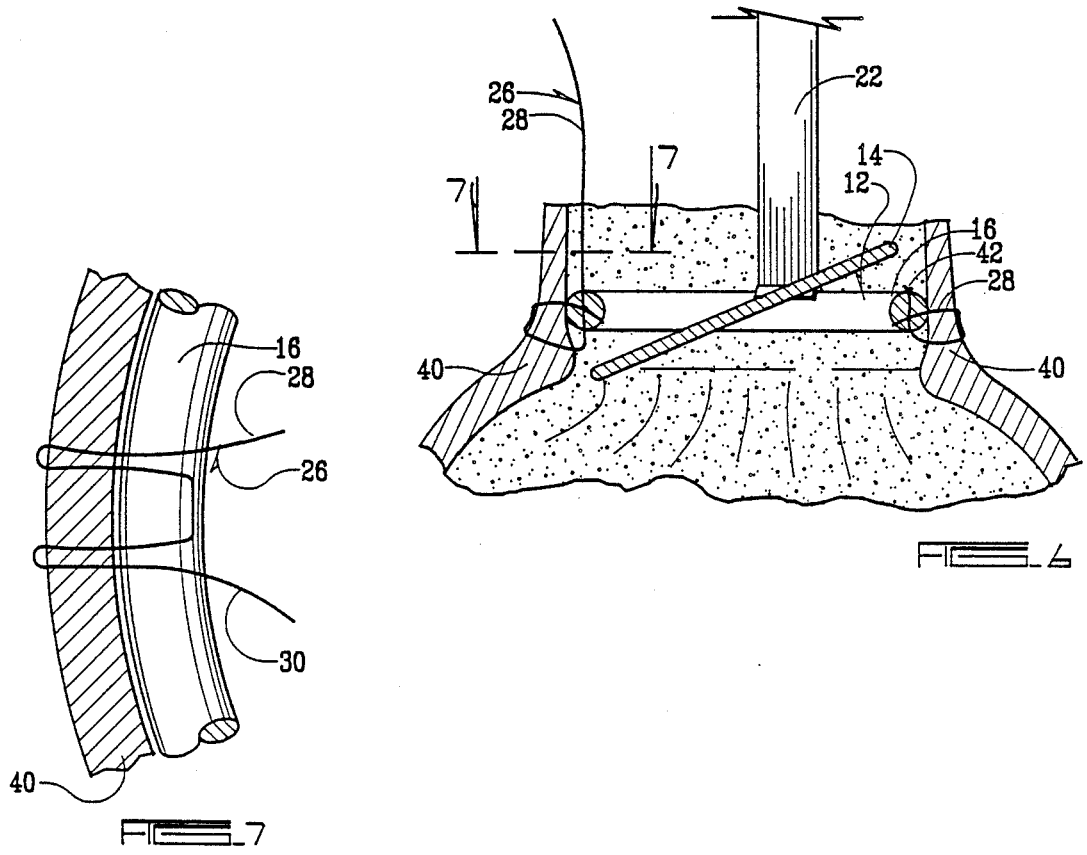

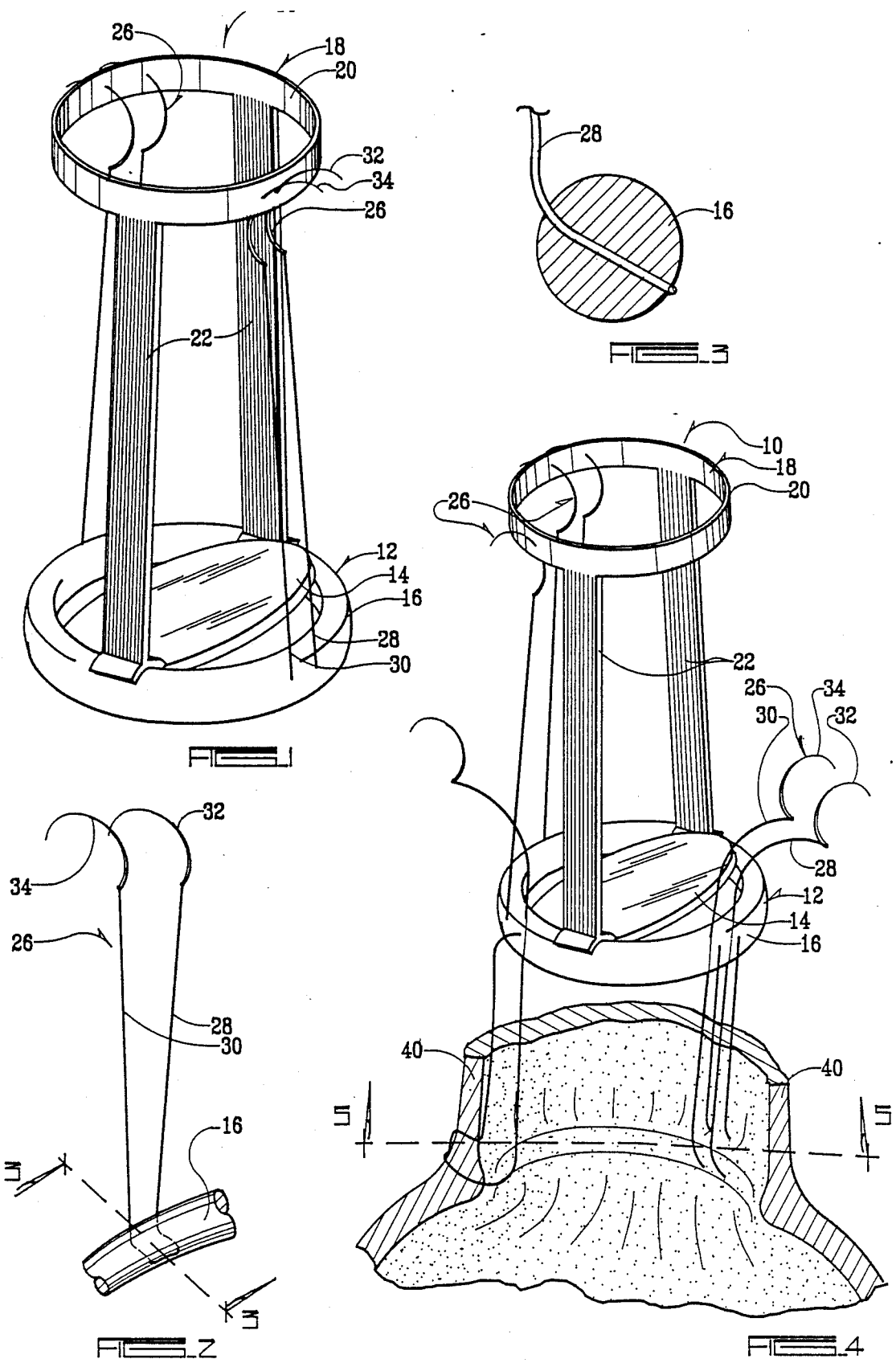

ARTIFICIAL VALVE, AND NEEDLE AND SUTURE HOLDER AND METHOD OF USING SAME

BACKGROUND OF THE INVENTION

Implantation of artificial valves are performed in a variety of different ways but basically adhere to the same basic principles. Generally, valve implantation techniques are performed in the following way. The natural valve and valve tissue are excised or excluded (occasionally the posterior leaflet of the mitral valve and the subvalvular mechanism are left intact—surgeon's choice). Following excision of the valve, sutures are placed into the annulus of the natural valve and then the same sutures are placed into the sewing ring of the artificial valve. The type of suture used, the use or non-use of pledgets, the type of stitch and the order in which the sutures are placed are unimportant (through the sewing ring of the artificial valve first or the annulus of the natural valve first).

SUMMARY OF THE INVENTION

The valve sewing ring of this invention eliminates one major step in valve replacements, i.e. implantation of the sutures through the sewing ring of the artificial valve, thereby reducing the implant time approximately 30–50%. The advantages of reducing the implant time to this degree are obvious and need not be explained. This technique is applicable to any type of valve, whether it be bioprosthetic or mechanical, of any design. The basic principle is as follows. The sewing ring of the valve to be implanted is commercially prepared with the sutures mounted within the sewing ring. Pairs of sutures, with needles attached, are arranged and spaced equally around the sewing ring. Individual pairs can be color coded in an alternating fashion (green versus white e.g.) for easier identification. In order to prevent the individual sutures and pairs of sutures from tangling, they are mounted on a special valve holder which will allow easy packaging, manipulation, and implantation.

A recommended technique for implantation of a valve containing the sutures mounted in the annulus is as follows. With the assistant holding the specially designed valve holder, each pair of needles are taken through the natural annulus of the excised valve in a vertical mattress fashion and then brought back in a mattress fashion through the appropriate level of the sewing ring of the artificial valve. This is done circumferentially and when all the sutures are placed through the natural annulus and the sewing ring of the valve, the valve is then seated and the pairs of sutures (each color) tied to each other. This eliminates the need for a pledget as the suture not only originates from, but also is tied over, the sewing ring. Following the appropriate number of knots, the ends are cut with the valve implanted.

DESCRIPTION OF THE DRAWINGS

FIG. 1 is a perspective view of the artificial valve, and needle and suture holder.

FIG. 2 is a fragmentary perspective view of a suture in the sewing ring.

FIG. 3 is a cross-sectional view taken along line 3—3 in FIG. 2.

FIG. 4 is fragmentary perspective view of the artificial valve, and needle and suture holder during the valve installation.

FIG. 5 is a cross-sectional view taken along line 5—5 in FIG. 4.

FIG. 6 is a cross-sectional view similar to FIG. 5 but showing the artificial valve seated in the annulus body tissue.

FIG. 7 is a cross-sectional view taken along line 7—7 in FIG. 6.

DESCRIPTION OF THE PREFERRED EMBODIMENT

The artificial valve, and needle and suture holder in this invention is referred to generally in FIG. 1 by the reference numeral 10. An artificial valve 12 includes a valve element 14 pivotally mounted in a cloth sewing ring 16.

A holder 18 includes a collar 20 having a handle leg means including oppositely disposed downwardly extending legs 22 with saddle-shaped ends which engage the top surface of the sewing ring 16 on opposite sides. A plurality of sutures 26 have opposite ends 28 and 30 with needles 32 and 34. Each suture 26 has a different color whereby opposite ends can be distinguished from each other when being tied together as will be described hereinafter.

Prior to the installation process, the holder is prepared for use during the operating procedure. The sutures 26 extend through the sewing ring 16, as seen in FIGS. 2 and 3, from the inside outwardly and thence upwardly to the holder collar 20 as seen in FIGS. 1 and 4 where the needles 32 and 34 engage the collar 20 to be temporarily held until needed during the installation procedure.

During the installation procedure an assistant would hold the holder 18 by the legs 22. Needle 32 would be removed from the collar 20 and then routed downwardly through the annulus 40 body tissue from the inside out and then back to the inside of the body tissue and thence upwardly through the sewing ring 16 as seen in FIG. 5. The same procedure is followed for the opposite end 30 of the suture 26. Upon all sutures 26 being in place as seen in FIG. 6 the sewing ring 16 is seated against the annulus 40 body tissue and the opposite ends 28 and 30, having a common color, are tied into a knot 42. The needles and excess suture material are cut away and discarded as seen on the right-hand side of FIG. 6. The valve 12 is now completely in place.

Thus it is seen that a greatly simplified procedure for installing heart artificial valves has been provided which will save approximately 30 to 50 percent of the ordinary time taken for this operation.

I claim:

1. An artificial valve, and needle and suture holder comprising,
   a valve having a valve means and a sewing ring with said valve means in the center of said sewing ring,
   a one piece needle and suture holder having a handle leg means, said handle leg means including oppositely disposed legs, each of said legs having oppositely ends with a collar integrally connected to one end and the other end directly engaging said sewing ring on opposite sides thereof for holding said collar in spaced relation to said sewing ring, and
   a plurality of sutures extending through said sewing ring and each suture having opposite ends to which needles are connected and held by said collar temporarily in spaced relation to said sewing ring in preparation for installing said artificial valve in a human, said sutures extending between said collar and said sewing ring being the only means for holding said sewing ring in engagement with said other ends of said oppositely disposed legs.

2. The structure of claim 1 wherein said sewing ring is cloth.

3. The structure of claim 1 wherein said sewing ring has an exterior annular edge and said suture ends extend outwardly through said sewing ring and then upwardly around the outside of said exterior annular edge of the sewing ring and thence upwardly to said collar.

4. The structure of claim 1 wherein said plurality of sutures having needles on opposite ends are spaced apart around said collar and said sutures are spaced apart around said sewing ring.

5. The structure of claim 4 wherein each of said sutures has a different color whereby needles for each suture on said holder can be easily identified during a valve operation.

6. The structure of claim 1 wherein said other end of said oppositely disposed legs are saddle shaped and matingly engage said sewing ring.

7. An artificial valve, and needle and suture holder comprising,
    a valve having a valve means and a sewing ring with said valve means in the center of said sewing ring,
    one piece needle and suture holder having a handle leg means, said handle leg means including oppositely disposed legs, each of said legs having opposite ends with a collar integrally connected to one end and the other end directly engaging said sewing ring on opposite sides thereof for holding said collar in spaced relation to said sewing ring,
    a plurality of sutures extending through said sewing ring and having opposite ends to which needles are connected and held by said collar in spaced relation to said sewing ring in preparation for installing said artificial valve in a human, said sutures extending between said collar and said sewing ring being the only means for holding said sewing ring in engagement with said other ends of said oppositely disposed legs,
    said sewing ring has an exterior annular edge and said suture ends extend outwardly through said sewing ring and then upwardly around the outside of said exterior annular edge of the sewing ring and thence upwardly to said collar where said needles are temporarily held by said collar until used in installing said valve in a human, and
    each of said sutures has a different color whereby needles for each suture on said holder can be easily identified during a valve operation.

8. The structure of claim 7 wherein said sutures extend through said sewing ring closely adjacent said valve.

9. The method of installing an artificial valve in a human body comprising the steps of,
    providing an artificial valve having a sewing ring, and a needle and suture holder wherein the opposite ends of a plurality of sutures extend through the sewing ring and upwardly with needles on the suture ends engaging said holder which is spaced from said valve,
    taking one needle on the end of one suture from said holder and passing it through the annular body tissue where the valve is to be installed and then extending the needle through the sewing ring,
    taking the other needle on the other end of the suture from the holder and passing it through the annular body tissue and then extending the needle through the sewing ring,
    taking the opposite ends of the other sutures and passing them through the annular body tissue and then extending the needles through the sewing ring, and
    tying the opposite ends of each suture together while positioning the valve and sewing ring in sealing engagement with the annular body tissue.

10. The method of claim 9 and the additional step of removing said needles on all of said sutures.

11. The method of claim 10 wherein when said sutures are provided, further providing sutures having different colors and then when said suture ends are tied, locating suture ends having like colors and tying them together.

* * * * *